(12) United States Patent
Temmei et al.

(10) Patent No.: US 9,384,547 B2
(45) Date of Patent: Jul. 5, 2016

(54) X-RAY IMAGE DIAGNOSTIC APPARATUS AND METHOD FOR CONTROLLING X-RAY GENERATION DEVICE

(75) Inventors: Konosuke Temmei, Tokyo (JP); Tadashi Nakamura, Tokyo (JP); Yuji Sakai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 186 days.

(21) Appl. No.: 14/232,338

(22) PCT Filed: Jul. 12, 2012

(86) PCT No.: PCT/JP2012/067789
§ 371 (c)(1),
(2), (4) Date: Jan. 13, 2014

(87) PCT Pub. No.: WO2013/011914
PCT Pub. Date: Jan. 24, 2013

(65) Prior Publication Data
US 2014/0140606 A1    May 22, 2014

(30) Foreign Application Priority Data

Jul. 19, 2011   (JP) .................. 2011-157919

(51) Int. Cl.
*A61B 6/00* (2006.01)
*G06T 7/00* (2006.01)
(Continued)

(52) U.S. Cl.
CPC ............... *G06T 7/0012* (2013.01); *A61B 6/542* (2013.01); *G06T 5/009* (2013.01); *G06T 5/40* (2013.01); *H05G 1/36* (2013.01); *G06T 2207/10116* (2013.01); *G06T 2207/30004* (2013.01)

(58) Field of Classification Search
USPC ........................................ 378/4, 62
See application file for complete search history.

(56) References Cited

U.S. PATENT DOCUMENTS

| 5,253,169 A * | 10/1993 | Corby, Jr. .............. A61B 6/12 |
| | | 382/132 |
| 6,215,846 B1 * | 4/2001 | Mazess .............. A61B 6/4225 |
| | | 348/E3.045 |

(Continued)

FOREIGN PATENT DOCUMENTS

| JP | 64/017631 | * | 1/1989 | ............... A61B 6/00 |
| JP | 2002312775 A | | 10/2002 | |

(Continued)

OTHER PUBLICATIONS

Anonymous: Otsu's Method—Wikipedia, the free encyclopedia, Mar. 14, 2011, XP055169774, retrieved from the Internet: URL:http://en.wikipedia.org/w/index.php?ti, 2 pages.

(Continued)

*Primary Examiner* — Chan Park
*Assistant Examiner* — Mia M Thomas
(74) *Attorney, Agent, or Firm* — Brundidge & Stanger, P.C.

(57) ABSTRACT

In order to follow the ABS conditions when the movement of the object position, such as the movement of an object or the movement of an X-ray tube, occurs during fluoroscopy, an X-ray image diagnostic apparatus includes a histogram generation unit 6b that generates a histogram showing the distribution of brightness values of an X-ray image of an object; an object region detection unit 6c that detects an object region, which is a region where the object is imaged, in the X-ray image on the basis of the histogram; and an X-ray condition determination unit 2a that determines X-ray conditions defining an output of X-rays so that a brightness value representing the object region approaches a target brightness value of the object region set in advance.

8 Claims, 9 Drawing Sheets

(51) Int. Cl.
 *H05G 1/36* (2006.01)
 *G06T 5/00* (2006.01)
 *G06T 5/40* (2006.01)

(56) References Cited

U.S. PATENT DOCUMENTS

| | | | | |
|---|---|---|---|---|
| 6,282,261 | B1* | 8/2001 | Mazess | A61B 6/4225 348/E3.045 |
| 6,315,445 | B1* | 11/2001 | Mazess | A61B 6/4225 348/E3.045 |
| 6,377,656 | B1* | 4/2002 | Ueki | A61B 6/4225 378/98.7 |
| 6,768,784 | B1* | 7/2004 | Green | A61B 6/00 378/62 |
| 6,839,457 | B1* | 1/2005 | Azuma | A61B 6/505 128/922 |
| 7,822,255 | B2* | 10/2010 | Schutz | H04N 5/32 382/132 |
| 9,014,455 | B2* | 4/2015 | Oh | A61B 6/52 378/98.11 |
| 2003/0165216 | A1 | 9/2003 | Walker | |
| 2004/0034269 | A1* | 2/2004 | Ozaki | A61N 5/1042 600/1 |
| 2004/0066897 | A1* | 4/2004 | Takahashi | A61B 6/504 378/98.7 |
| 2005/0207630 | A1* | 9/2005 | Chan | A61B 6/466 382/131 |
| 2006/0008048 | A1* | 1/2006 | Katada | A61B 6/032 378/16 |
| 2006/0109958 | A1* | 5/2006 | Ertel | A61B 6/08 378/205 |
| 2007/0003123 | A1* | 1/2007 | Fu | A61N 5/1049 382/131 |
| 2007/0025607 | A1* | 2/2007 | Takaishi | A61B 6/14 382/132 |
| 2007/0058772 | A1* | 3/2007 | Schutz | H04N 5/32 378/4 |
| 2008/0253637 | A1* | 10/2008 | Boyden | A61B 6/145 382/131 |
| 2009/0129658 | A1 | 5/2009 | Takahashi | |
| 2009/0190819 | A1* | 7/2009 | Fischer | A61B 6/022 382/132 |
| 2011/0188723 | A1* | 8/2011 | Bruder | A61B 6/032 382/131 |
| 2013/0057569 | A1* | 3/2013 | Liao | G06T 3/0068 345/589 |
| 2014/0093128 | A1* | 4/2014 | Teshima | G06T 5/009 382/103 |
| 2015/0071406 | A1* | 3/2015 | Temmei | A61B 6/469 378/62 |
| 2015/0235725 | A1* | 8/2015 | Makifuchi | G21K 1/067 378/87 |
| 2015/0310597 | A1* | 10/2015 | Ohguri | G06T 5/50 382/275 |

FOREIGN PATENT DOCUMENTS

| | | |
|---|---|---|
| JP | 2005245734 A | 9/2005 |
| JP | 2009119055 A | 6/2009 |

OTHER PUBLICATIONS

European Search Report dated Feb. 25, 2015, 8 pages.

* cited by examiner

| OBJECT THICKNESS | TUBE CURRENT / TUBE VOLTAGE | $PV_{ABS}$ | FEEDBACK VOLTAGE |
|---|---|---|---|
| 20 cm | $mA_{20} / kV_{20}$ | $X_3$ | $Y_3 [V]$ |
| 10 cm | $mA_{20} / kV_{20}$ | $X_4$ | $Y_4 [V]$ |

(b)

| OBJECT THICKNESS | TUBE CURRENT / TUBE VOLTAGE | $PV_{ABS}$ | FEEDBACK VOLTAGE |
|---|---|---|---|
| 20 cm | $mA_{20} / kV_{20}$ | $X_3$ | $Y_3 [V]$ |
| 10 cm | $mA_{10} / kV_{10}$ | $X_3$ | $Y_3 [V]$ |

X-RAY IMAGE DIAGNOSTIC APPARATUS AND METHOD FOR CONTROLLING X-RAY GENERATION DEVICE

TECHNICAL FIELD

The present invention relates to an X-ray image diagnostic apparatus and a method for controlling an X-ray generation device and, in particular, to controlling the brightness of an X-ray image.

BACKGROUND ART

Some X-ray image diagnostic apparatuses have an Automatic Brightness control System (hereinafter, abbreviated as "ABS") that controls a tube voltage automatically so that the brightness of a fluoroscopic image is always constant even if an object thickness is changed. As an example of the ABS, there is a system that sets a region of interest (hereinafter, abbreviated as "ROI") for an image region output from an X-ray detector and controls a tube voltage automatically such that a value of a feedback signal approaches a reference value set in advance using an average brightness value in the ROI as the feedback signal. As an example of a control method, for example, when the feedback signal is lower than the reference value, the tube voltage acts in an increasing direction. As the tube voltage increases, the X-ray output increases. Accordingly, the next fluoroscopic image becomes an image having a higher brightness than an image before the increase.

However, when the position of the ROI is fixed, if the living tissue of an object that an operator desires to see deviates from the ROI for some reasons, such as the position movement of the object, an appropriate feedback signal is not calculated. Accordingly, it is not possible to obtain the preferred image quality.

In order to eliminate the undesirable effect described above, PTL 1 discloses a fluoroscopic apparatus that sets an ROI freely with a pointing device, such as a mouse, during X-ray fluoroscopic imaging and feeds the result back to the ABS using image data in the ROI.

CITATION LIST

Patent Literature

[PTL 1] JP-T-2005-522237

SUMMARY OF INVENTION

Technical Problem

In the method disclosed in PTL 1, however, when the movement of the object position, such as the movement of the object or the movement of the X-ray tube, occurs during fluoroscopic imaging and a part of interest deviates from the ROI causing deviation from the appropriate X-ray conditions, the operator needs to reset and update the position and size of the ROI as necessary. This lowers the examination efficiency.

The present invention has been made in view of the above-described problem, and it is an object of the present invention to provide an X-ray image diagnostic apparatus, in which an ABS system that follows the movement of the object position without performing an ROI setting operation by an operator is mounted, and a method for controlling an X-ray generation device.

Solution to Problem

In order to solve the aforementioned problem, in the present invention, a histogram showing the distribution of brightness values of an X-ray image of an object is generated, an object region that is a region where the object is imaged in the X-ray image is detected using the generated histogram, and X-ray conditions defining an output of X-rays are determined so that a brightness value of the detected object region approaches a target brightness value set in advance.

Advantageous Effects of Invention

According to the present invention, since ABS control can be performed by calculating the feedback value so as to follow the movement of the object position without performing an ROI setting operation by the operator, it is possible to omit the time and effort of the operator.

DESCRIPTION OF EMBODIMENTS

Hereinafter, an embodiment to which the present invention is applied will be described.

An X-ray image diagnostic apparatus of the present invention is an X-ray image diagnostic apparatus including: an X-ray generation unit that generates X-rays according to X-ray conditions defining an output of X-rays; an X-ray detection unit that detects X-rays transmitted through an object and outputs a transmitted X-ray signal; and an image generation unit that generates an X-ray image of the object on the basis of the transmitted X-ray signal. The X-ray image diagnostic apparatus includes a histogram generation unit that generates a histogram showing a distribution of brightness values of the X-ray image; an object region detection unit that detects an object region, which is a region where the object is imaged, in the X-ray image on the basis of the histogram; and an X-ray condition determination unit that determines the X-ray conditions so that a brightness value representing the object region approaches a target brightness value of the object region set in advance. The X-ray generation unit generates the X-rays according to the determined X-ray conditions.

In addition, the object region detection unit divides the histogram into two data groups with an arbitrary brightness value as a boundary, sets, as a first threshold value, a brightness value when an inter-class variance of two classes of the respective data groups or an index value increasing or decreasing in association with the inter-class variance is maximized, and detects a data group less than the first threshold value as the object region.

In addition, the histogram generation unit generates a processed histogram by performing at least one of processing of reducing a gradation to the arbitrary number of bits, which is less than the number of bits of the X-ray image, and processing of thinning out a histogram generated from the X-ray image with a predetermined brightness value, and the object region detection unit detects the object region using the processed histogram.

In addition, a feedback brightness value calculation unit is further provided that sets, as a reference brightness value, a brightness value when a ratio of the total number of pixels added from a minimum brightness value in the histogram to the total number of pixels of the histogram reaches a second threshold value set in advance and calculates, as a feedback brightness value, a value obtained by dividing a sum of values, which are obtained by multiplying respective brightness values from the minimum brightness value to the reference brightness value by the number of pixels of the corresponding brightness value, by a sum of the number of pixels from the minimum brightness value to the reference brightness value. The X-ray condition determination unit determines the X-ray conditions so that the feedback brightness value matches the target brightness value.

In addition, an object region ratio calculation unit that calculates a ratio of the number of pixels of the object region to the total number of pixels of the histogram is further provided. The feedback brightness value calculation unit determines to which of at least two or more image types having different object region ratios the X-ray image corresponds according to the calculated object region ratio, and determines the second threshold value according to each image type.

In addition, the image type and the second threshold value according to each image type are determined according to at least one of a procedure of capturing the X-ray image or a part for which the X-ray image is to be captured.

In addition, the feedback brightness value calculation unit calculates the feedback brightness value with a brightness value of a region where a metal is imaged in the histogram as the minimum brightness value.

In addition, a feedback voltage calculation unit that calculates a feedback voltage by converting the feedback brightness value into a voltage is further provided. The X-ray condition determination unit compares a reference voltage, which is obtained by converting the target brightness value into a voltage, with the feedback voltage, and changes the X-ray conditions so that the output of the X-rays is increased when the feedback voltage is lower than the reference voltage and changes the X-ray conditions so that the output of the X-rays is reduced when the feedback voltage is higher than the reference voltage.

In addition, the histogram generation unit generates a histogram showing a distribution of brightness values of a region on an inner side than a region, in which an X-ray aperture to limit an irradiation region of X-rays is imaged, in the X-ray image.

In addition, a method for controlling an X-ray generation device of the present invention includes: a step of generating a histogram showing a distribution of brightness values of an X-ray image of an object; a step of detecting an object region, which is a region where the object is imaged, in the X-ray image on the basis of the histogram; and a step of determining X-ray conditions defining an output of X-rays so that a brightness value representing the object region approaches a target brightness value of the object region set in advance.

Figure 1:
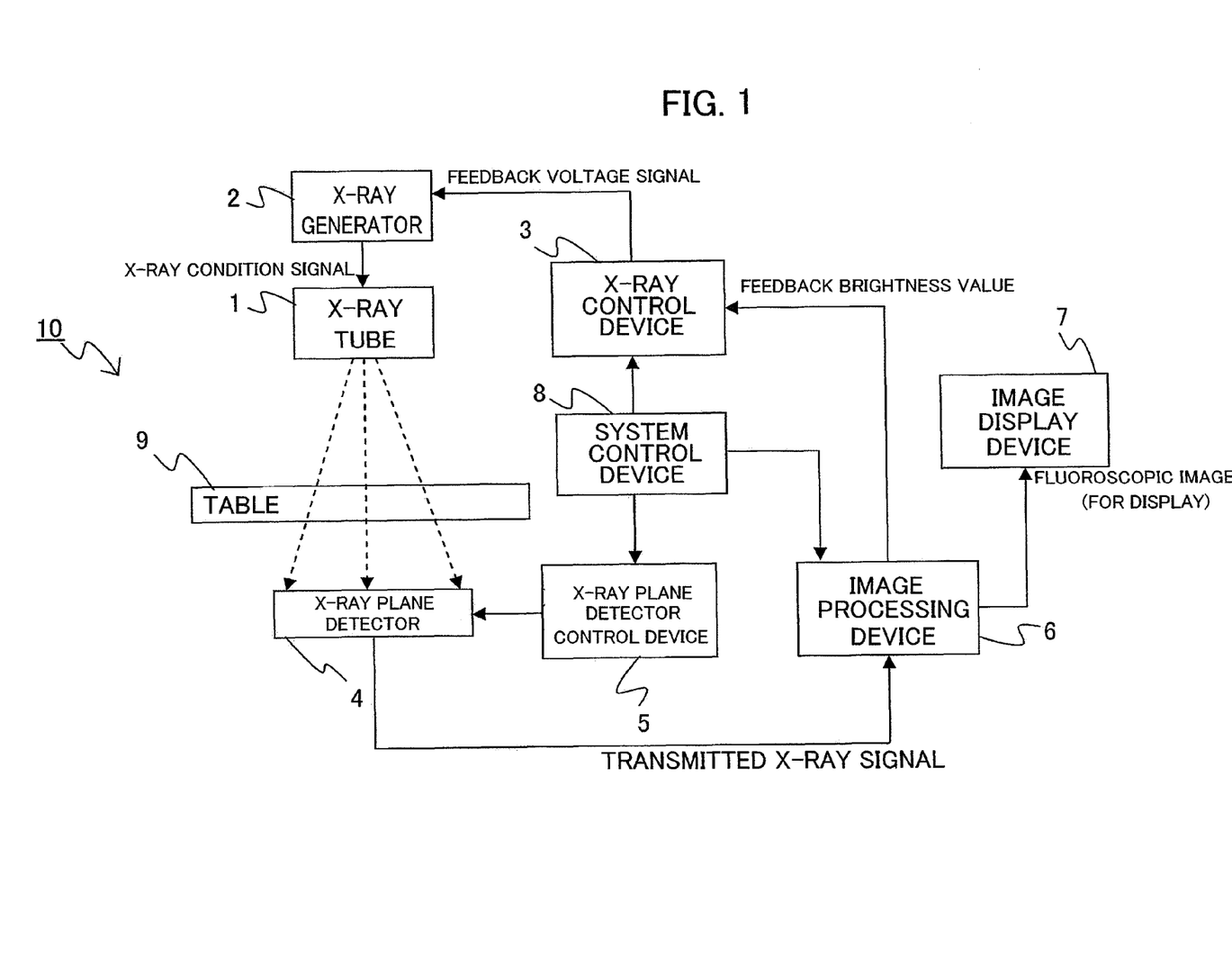
FIG. 1 is a block diagram showing the configuration of an X-ray image diagnostic apparatus according to the present embodiment.
Figure 2:
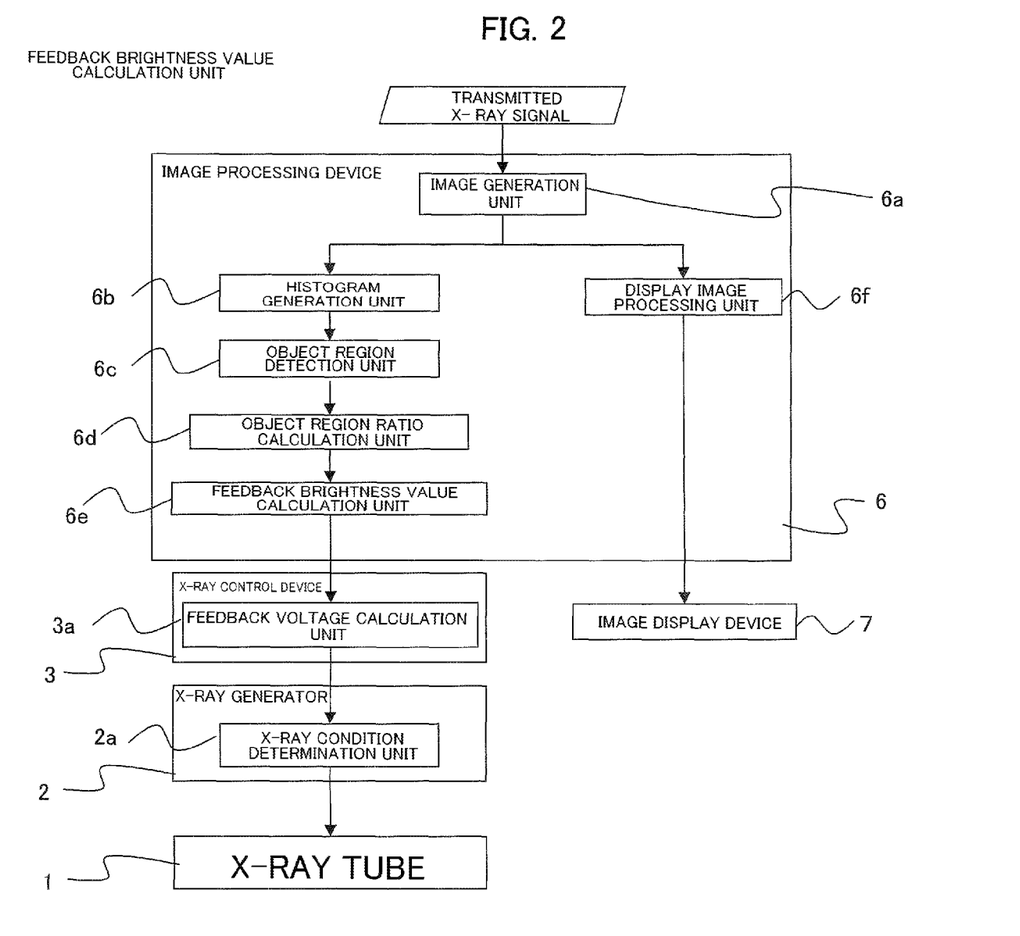
FIG. 2 is a functional block diagram of an X-ray fluoroscopic apparatus according to the present embodiment.

Next, an embodiment of the present invention will be described in detail with reference to the diagrams. Components having the same functions and procedures of the same processing content are denoted by the same reference numerals, and explanation thereof will be omitted. In the present embodiment, a case where the present invention is applied to an X-ray fluoroscopic apparatus 10 that generates an X-ray image (hereinafter, referred to as a "fluoroscopic image") of a dynamic image will be described as an example. However, the present invention can be applied to an X-ray image imaging apparatus that images a still image, to adjust the brightness of the still image or to an X-ray image diagnostic apparatus that performs both fluoroscopy and imaging. Hereinafter, the schematic configuration of the X-ray fluoroscopic apparatus according to the present embodiment will be described with reference to FIGS. 1 and 2. FIG. 1 is a block diagram showing the configuration of the X-ray fluoroscopic apparatus according to the present embodiment. FIG. 2 is a functional block diagram of the X-ray fluoroscopic apparatus according to the present embodiment.

As shown in FIG. 1, the X-ray fluoroscopic apparatus 10 according to the present embodiment includes: an X-ray tube 1 that generates X-rays; an X-ray generator 2 that outputs an X-ray condition signal (for example, signals showing a tube current value and a tube voltage value) to the X-ray tube 1; an X-ray control device 3 that transmits a feedback voltage signal for determining X-ray conditions to the X-ray generator 2; an X-ray plane detector 4 that is disposed opposite the X-ray tube 1 and detects X-rays transmitted through an object; an X-ray plane detector control device 5 that controls reading processing of the detected transmitted X-ray signal; an image processing device 6 that generates a fluoroscopic image on the basis of the read transmitted X-ray signal, calculates a feedback brightness value on the basis of the fluoroscopic image, and outputs the feedback brightness value to the X-ray control device 3; an image display device 7 that displays a fluoroscopic image; a system control device 8 that controls the X-ray control device 3, the X-ray plane detector control device 5, and the image processing device 6; and a table 9 on which the object is placed.

As shown in FIG. 2, the image processing device 6 includes: an image generation unit 6a that generates a fluoroscopic image on the basis of the transmitted X-ray signal output from the X-ray plane detector control device 5; a histogram generation unit 6b that generates a histogram showing the distribution of pixel values of each frame of the generated fluoroscopic image; an object region detection unit 6c that detects a region where an object occupied in each frame is imaged (hereinafter, referred to as an "object region") on the basis of the histogram; an object region ratio calculation unit 6d that calculates an occupation ratio of the calculated object region to the entire fluoroscopic image; a feedback brightness value calculation unit 6e that calculates a feedback brightness value under the conditions corresponding to the object ratio; and a display image processing unit 6f that performs gradation processing for displaying the fluoroscopic image generated by the image generation unit 6a on the image display device 7 and outputs image data for display to the image display device 7. That is, the image processing device 6 is largely divided into an arithmetic processing unit for ABS control (histogram generation unit 6b, object region detection unit 6c, object region ratio calculation unit 6d, and feedback brightness value calculation unit 6e) and a display processing unit for image display (display image processing unit 6f).

On the other hand, the X-ray control device 3 includes a feedback voltage calculation unit 3a that converts the feedback brightness value received from the image processing device 6 into a voltage (hereinafter, referred to as a "feedback voltage").

In addition, the X-ray generator 2 includes an X-ray condition determination unit 2a that determines the X-ray conditions (tube current and tube voltage) so that the feedback voltage received from the X-ray control device 3 becomes a fixed value set in advance to obtain the object region of the fluoroscopic image having a desired brightness value (hereinafter, referred to as a "target brightness value"). In the present embodiment, a reference voltage obtained by converting the target brightness value into a voltage is used as the fixed value.

The image generation unit 6a, the histogram generation unit 6b, the object region detection unit 6c, the object region ratio calculation unit 6d, the feedback brightness value calculation unit 6e, the display image processing unit 6f, the feedback voltage calculation unit 3a, and the X-ray condition determination unit 2a are formed by a program for realizing the functions of these units and a hardware apparatus that loads and executes the program.

First Embodiment

Figure 3:
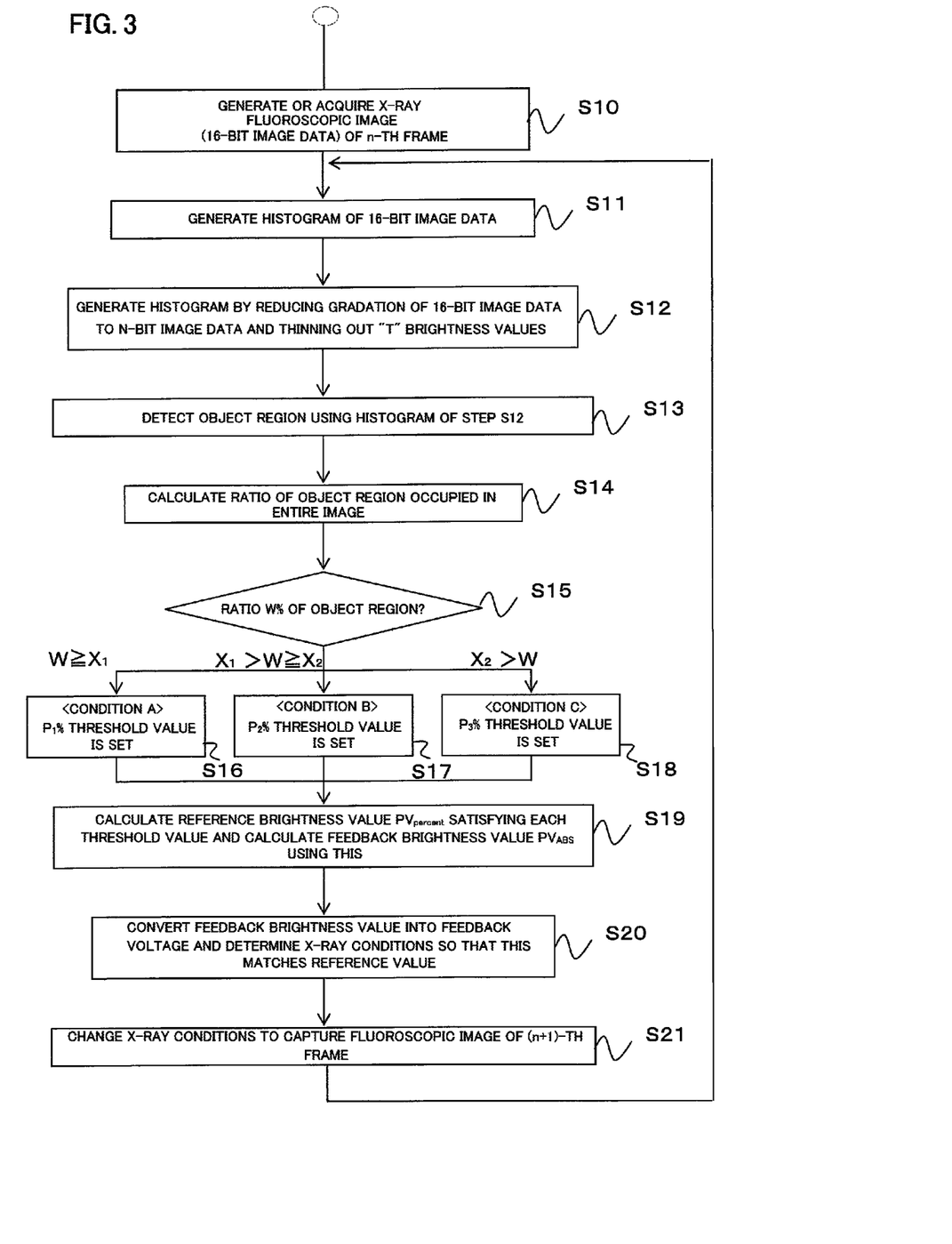
FIG. 3 is a flow chart showing the flow of the process of ABS control according to the present embodiment.
Figure 4:
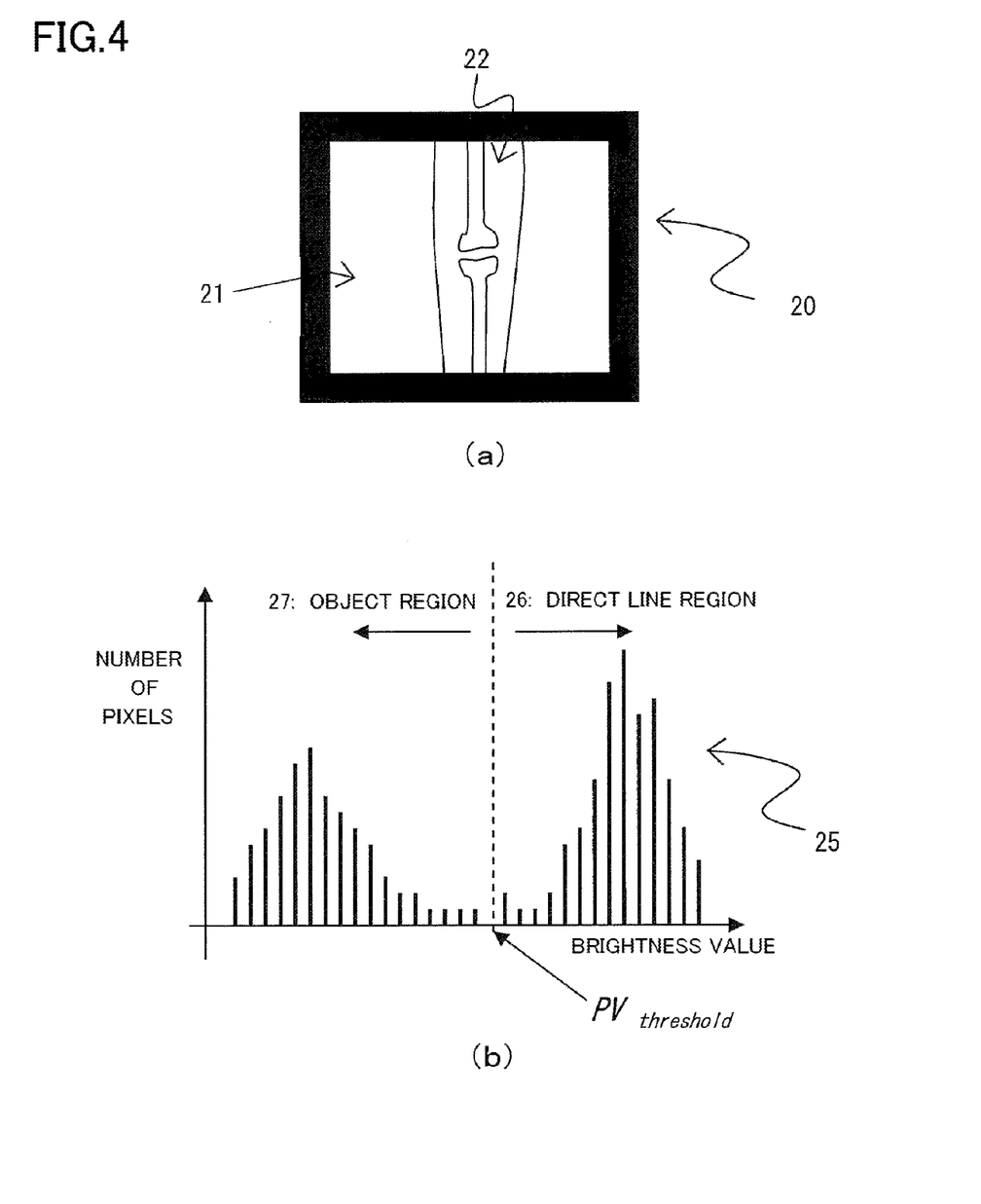
FIG. 4 is an explanatory diagram showing a fluoroscopic image and a histogram generated on the basis of the fluoroscopic image, where (a) shows an example of the fluoroscopic image and (b) shows a histogram obtained by reducing the gradation of the histogram of the fluoroscopic image to N bits and thinning out "T" brightness values.
Figure 5:
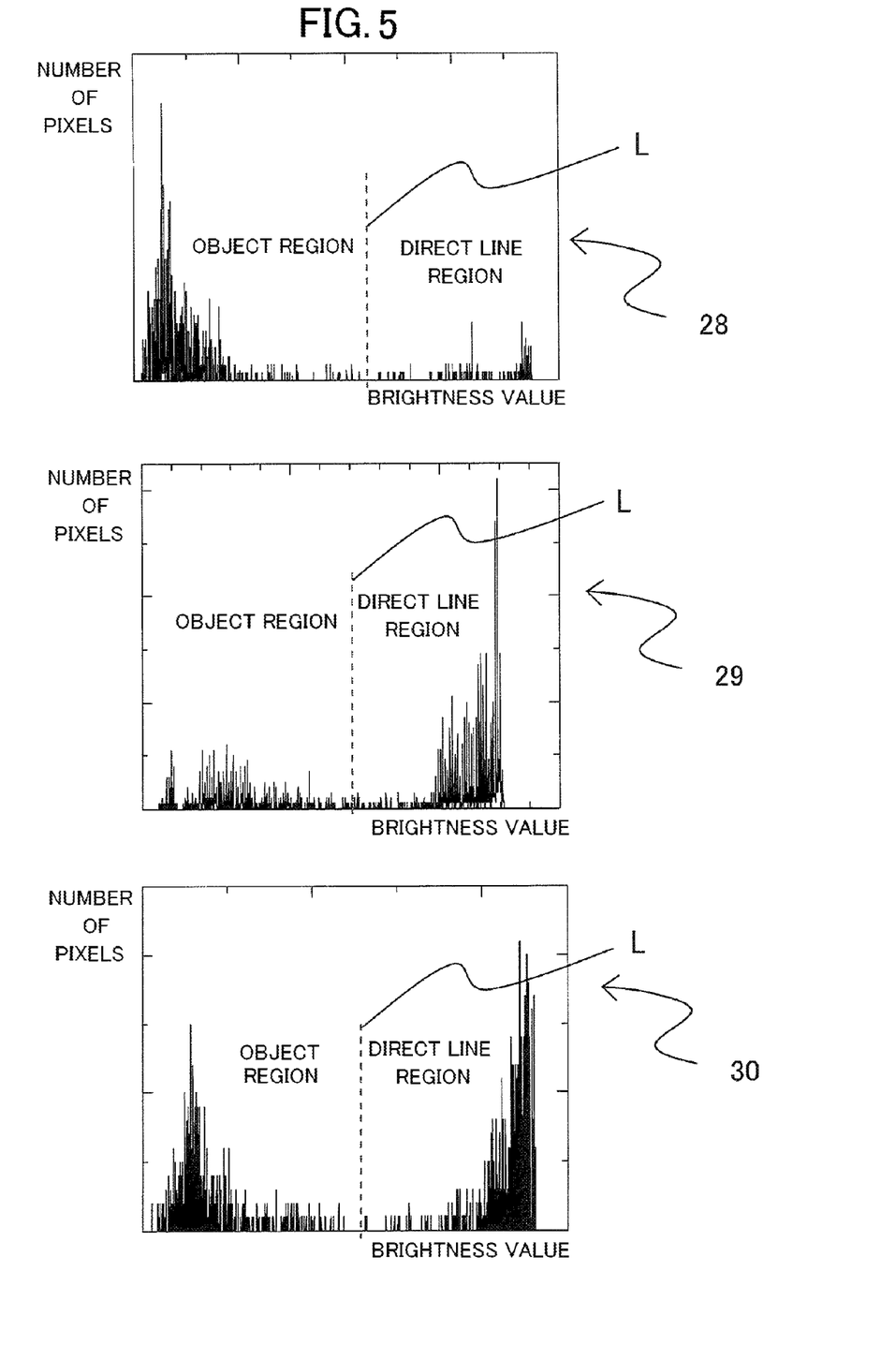
FIG. 5 is an explanatory diagram showing a histogram of an image corresponding to each image pattern.
Figure 6:
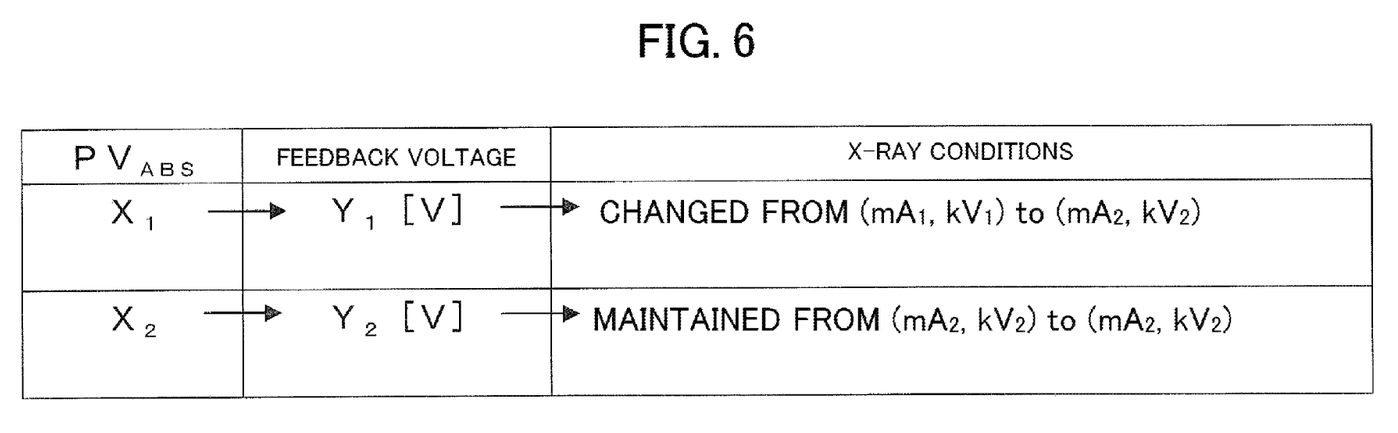
FIG. 6 is an explanatory diagram showing the process of conversion from a feedback brightness value to X-ray conditions.
Figure 7:
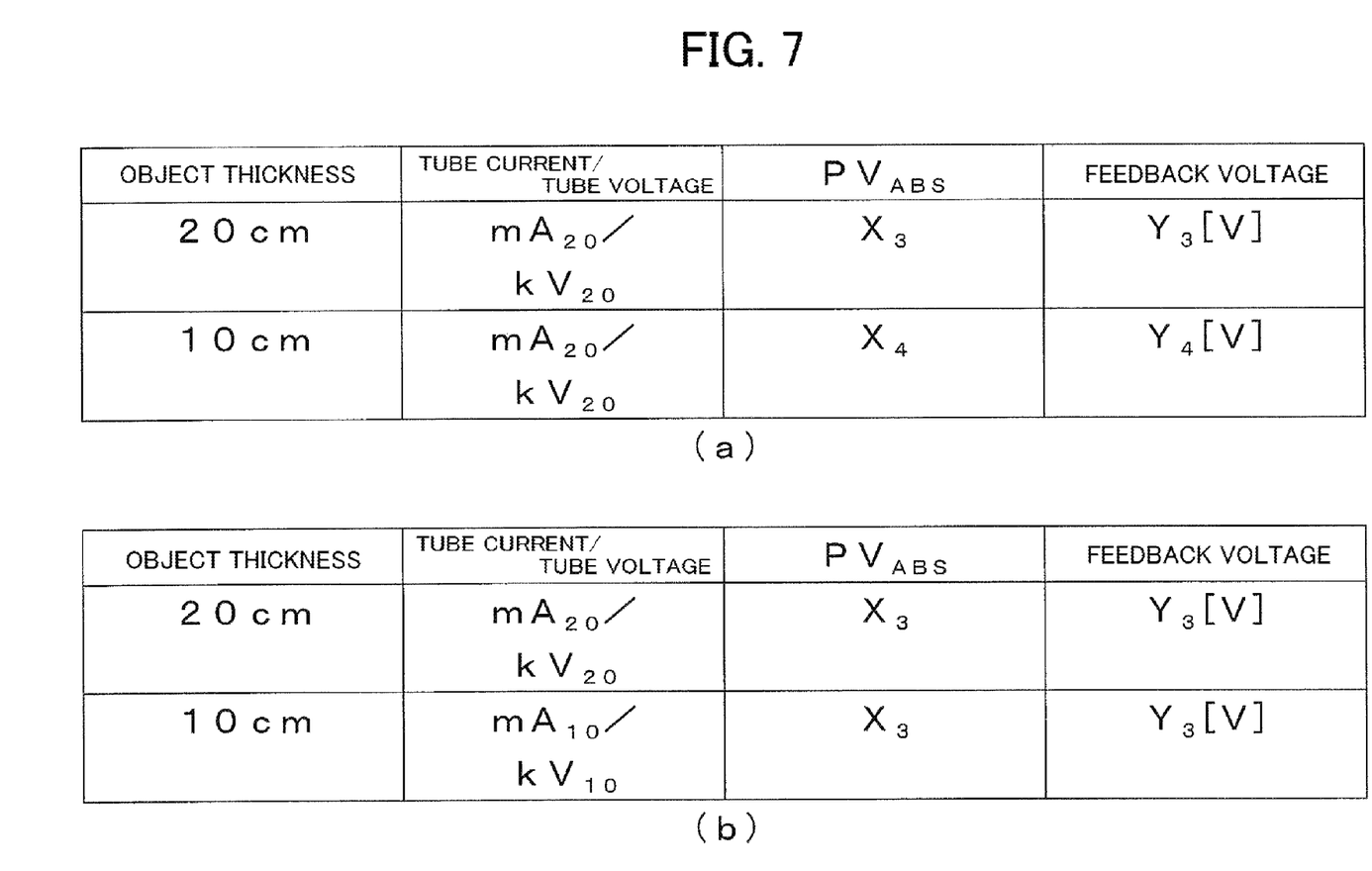
FIG. 7 is an explanatory diagram showing the relationship between the feedback brightness value and the X-ray conditions (tube current/tube voltage), where (a) shows the relationship among the object thickness, X-ray conditions (tube current/tube voltage), feedback brightness value, and feedback voltage when performing irradiation under the same X-ray conditions for different object thicknesses and (b) shows the relationship among the object thickness, X-ray conditions (tube current/tube voltage), feedback brightness value, and feedback voltage when the ABS functions for different object thicknesses.
Figure 8:
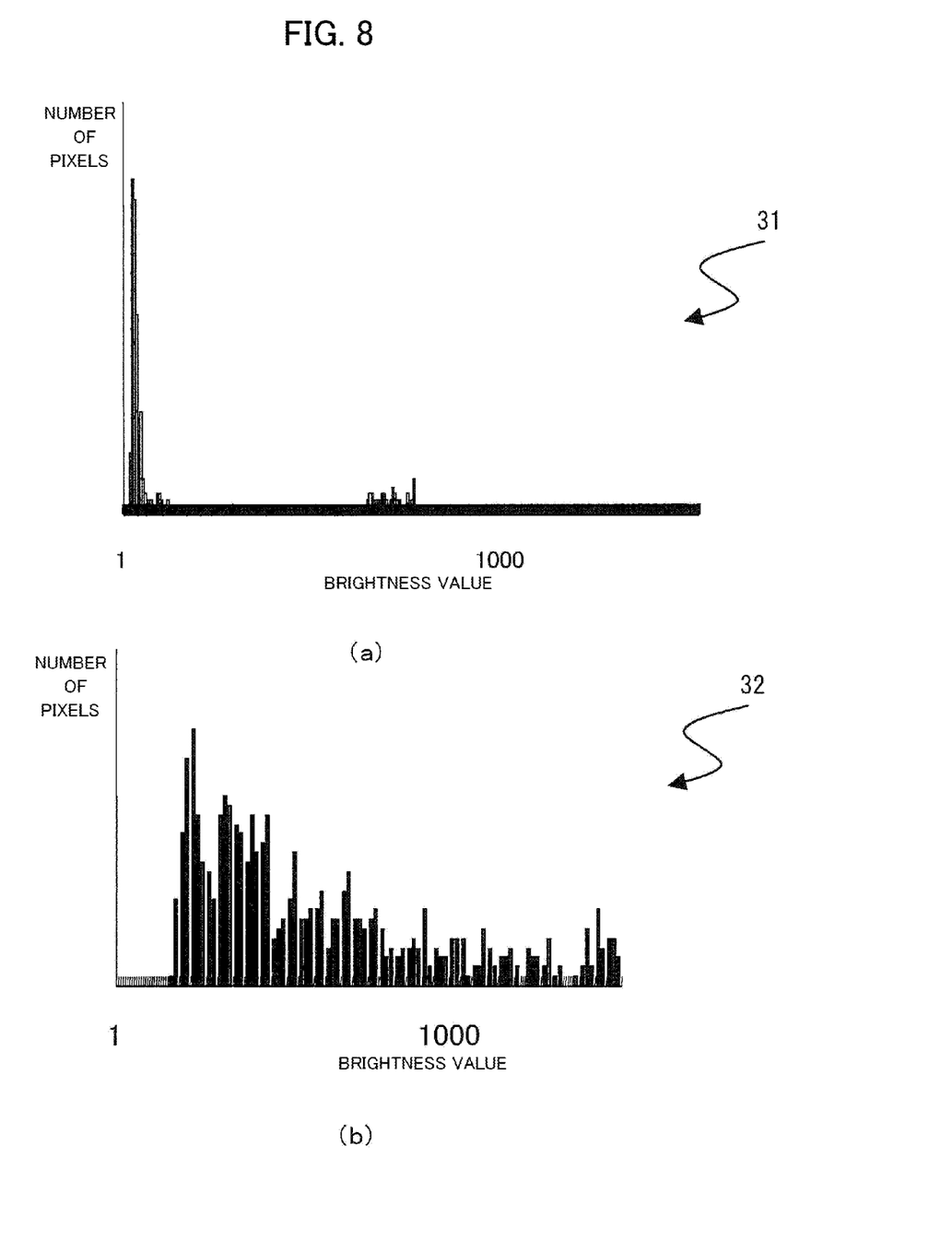
FIG. 8 is an explanatory diagram for explaining the effect of ABS control, where (a) shows a histogram when the feedback brightness value is lower than the target brightness value and (b) shows a histogram when the feedback brightness value becomes the target brightness value.

Here, a first embodiment will be described with reference to FIGS. 3 to 8. FIG. 3 is a flow chart showing the flow of the process of ABS control according to the embodiment. FIG. 4 is an explanatory diagram showing a fluoroscopic image and a histogram generated on the basis of the fluoroscopic image, where (a) shows an example of the fluoroscopic image and (b) shows a histogram obtained by reducing the gradation of the histogram of the fluoroscopic image to N bits and thinning out "T" brightness values. FIG. 5 is an explanatory diagram showing a histogram of an image corresponding to each image pattern. FIG. 6 is an explanatory diagram showing the process of conversion from the feedback brightness value to X-ray conditions. FIG. 7 is an explanatory diagram showing the relationship between the feedback brightness value and the X-ray conditions (tube current/tube voltage), where (a) shows the relationship among the object thickness, X-ray conditions (tube current/tube voltage), feedback brightness value, and feedback voltage when performing irradiation under the same X-ray conditions for different object thicknesses and (b) shows the relationship among the object thickness, X-ray conditions (tube current/tube voltage), feedback brightness value, and feedback voltage when the ABS functions for different object thicknesses. FIG. 8 is an explanatory diagram for explaining the effect of ABS control, where (a) shows a histogram when the feedback brightness value is lower than the target brightness value and (b) shows a histogram when the feedback brightness value becomes the target brightness value.

When fluoroscopy is started, a fluoroscopic X-ray signal is read from the X-ray plane detector 4 according to the read signal of the X-ray plane detector control device 5 and is transmitted to the image processing device 6. Hereinafter, explanation will be given along respective steps in FIG. 3.

(Step S10)

In step S10, the image generation unit 6a acquires a transmitted X-ray signal as a basis of an n-th frame from the X-ray plane detector 4, and generates 16-bit fluoroscopic image data (S10). In the present embodiment, the 16-bit fluoroscopic image data is output to the histogram generation unit 6b for ABS control and is also output to the display image processing unit 6f for display gradation processing. Alternatively, it is also possible to acquire 16-bit fluoroscopic image data already generated.

(Step S11)

In step S11, the histogram generation unit 6b generates a histogram using the 16-bit fluoroscopic image data (S11).

(Step S12)

The object region detection unit 6c reduces the gradation of the fluoroscopic image data from 16 bits to N bits, and performs processing of thinning out "T" brightness values. Then, a histogram showing the distribution of brightness values after gradation reduction and thinning is generated (S12). In this case, N bits are an arbitrary gradation less than 16 bits. Therefore, when the histogram gradation is reduced from 16 bits to N bits, the brightness value of an arbitrary pixel in the fluoroscopic image data is converted as in the following Expression (1).

$$PV_{Nbit} = PV_{16bit} \div 2^{(16-N)} \tag{1}$$

$PV_{Nbit}$: brightness value of arbitrary pixel after reduction of gradation to N bits
$PV_{16bit}$: brightness value of arbitrary pixel at the time of 16 bits The purpose of reducing the histogram gradation in this step is to speedup the calculation of the discriminant analysis method performed in step S13. In the discriminant analysis method, the calculation time depends on the brightness value width of the histogram from the calculation algorithm. Therefore, the calculation time is shortened by reducing the gradation to reduce the brightness value width.

In addition, as a further reduction in the calculation time, a further increase in the speed becomes possible by thinning out "T" brightness values on the histogram, in which the gradation has been reduced to N bits, at equal intervals.

Since the processing of reducing the gradation to N bits and the thinning processing performed in this step are not essential, these processes may be omitted. In this case, the process proceeds to step S13 from step S11.

(Step S13)

The object region ratio calculation unit 6d detects an object region on the basis of the histogram after reducing the gradation to N bits and thinning out the brightness values by "T" (S13). In this step, the histogram is divided into two parts with an arbitrary brightness value, which is present on the histogram after reducing the gradation to N bits and thinning out "T" brightness values, as a boundary, and a brightness value that maximizes an inter-class variance when the two parts are set to a class 1 and a class 2, respectively, is calculated as a threshold value. Specifically, a brightness value $PV_{threshold}$ when the value of an inter-class variance $\Delta 1$ calculated from the following Expression (2) is maximized is calculated.

$$\Delta 1 = \{\omega_1(\mu_1 - \mu_a)^2 + \omega_2(\mu_2 - \mu_a)^2\}/(\omega_1 + \omega_2) \tag{2}$$

$\Delta 1$: value of inter-class variance
$\omega_1$: number of pixels of class 1
$\omega_2$: number of pixels of class 2
$\mu_1$: average brightness value of class 1
$\mu_2$: average brightness value of class 2
$\mu_a$: average brightness value of entire image In addition, the denominator $(\omega_1 + \omega_2)$ on the right side of Expression (2) shows the total number of pixels of one fluoroscopic image (that is, a fluoroscopic image of one frame), and this value is the same in all frames that form the fluoroscopic image. Accordingly, when calculating the brightness value $PV_{threshold}$ when the inter-class variance Δ1 is maximized, the following Expression (2-1) may be used by omitting the division operation using $(\omega_1+\omega_2)$ on the right side of Expression (2). Expression (2-1) is an expression of calculating an index value Δ2 associated with the inter-class variance, but the inter-class variance Δ1 is also maximized when Δ2 is maximized. By using Expression (2-1) instead of Expression (2), the division operation using $(\omega_1+\omega_2)$ can be omitted. As a result, it is possible to perform calculation processing at higher speed.

$$\Delta 2 = \omega_1(\mu_1-\mu_a)^2 + \omega_2(\mu_2-\mu_a)^2 \quad (2\text{-}1)$$

Δ2: index value associated with value of inter-class variance $\omega_1$: number of pixels of class 1
$\omega_2$: number of pixels of class 2
$\mu_1$: average brightness value of class 1
$\mu_2$: average brightness value of class 2
$\mu_a$: average brightness value of entire image (a) of FIG. 4 shows a fluoroscopic image 20 displayed on the image display device 7, and (b) is a histogram 25 obtained by reducing the gradation of a histogram, which shows the distribution of the pixel values of the 16-bit fluoroscopic image 20, to N bits and thinning out "T" brightness values. Similar to the histogram 25, a histogram showing the distribution of all pixel values of the fluoroscopic image 20 of 16-bit data also shows a bimodal due to a difference in the pixel value between a direct line region 21 and an object region 22.

The fluoroscopic image 20 includes the direct line region 21 where X-rays are directly incident on the X-ray plane detector 4 and the object region 22 on which X-rays transmitted through the object are incident. The histogram 25 of the fluoroscopic image 20 has a bimodal that mainly includes a region where high brightness values of pixels forming the direct line region 21 are distributed and a region where brightness values of pixels forming the object region 22 are distributed. In this case, the brightness value $PV_{threshold}$ at which the inter-class variance is maximized becomes a portion of the valley between two mountains. Accordingly, a data group of the brightness value equal to or greater than $PV_{threshold}$ can be recognized as a direct line region 26, and a data group of the brightness value less than $PV_{threshold}$ can be recognized as an object region 27.

(Step S14)

The object region ratio calculation unit 6d calculates the direct line region 26 by calculating $PV_{threshold}$ on the basis of the histogram 25. Then, the object region ratio calculation unit 6d calculates a ratio W (%) of the object region 27 to the entire histogram 25 on the basis of the following Expression (3) (S14).

$$W(\%) = C_{sp} \div C_{all} \quad (3)$$

W: ratio of object region 27 calculated for entire histogram 25
$C_{sp}$: number of pixels of object region 27 in histogram
$C_{all}$: number of pixels of entire histogram 25

(Step S15)

The feedback brightness value calculation unit 6e performs classification into a plurality of image patterns according to the object region ratio on the basis of the ratio W (%) of the object region 27 calculated by the object region ratio calculation unit 6d (S15). In this step, an image having an object region ratio equal to or higher than $X_1$ is defined as an image having a high object region ratio, an image having an object region ratio equal to or higher than $X_2$ and less than $X_1$ is defined as an intermediate image, and an image having an object region ratio less than $X_2$ is defined as an image having a low object region ratio. By comparing the ratio W (%) of the object region 27 with the conditions used in each definition, conditional branching is performed to determine which of the three image patterns a focused image matches (S15). The process proceeds to step S16 in the case of the image having a high object region ratio, proceeds to step S17 in the case of the intermediate image, and proceeds to step S18 in the case of the image having a low object region ratio.

(Steps S16 to S18)

The feedback brightness value calculation unit 6e sets values of $P_1$, $P_2$, and $P_3$ used in the calculation of the P tile method, which are determined according to each image pattern (S16 to S18). Details of the P tile method will be described in the following step S19.

The above values of $P_1$, $P_2$, and $P_3$ are determined by calculating the optimal X-ray outputs of the respective image patterns (in the present embodiment, three image patterns of an image having a relatively large object region, an intermediate image, and an image having a relatively small object region) experimentally in advance and performing an adjustment to be the same as the outputs.

Here, $P_1$ is a value calculated from the image pattern having a relatively high object region ratio, in which the object region W (%) equal to or greater than $X_1$ is included. $P_2$ is a value calculated from the intermediate image pattern in which the object region W (%) equal to or greater than $X_2$ and less than $X_1$ is included. $P_3$ is a value calculated from the image pattern having a relatively low object region ratio, in which the object region W (%) less than $X_2$ is included. FIG. 5 shows a histogram of each image pattern.

A dotted line L in each histogram shows $PV_{threshold}$. A histogram 28 is a histogram of an image having a high object region ratio in a fluoroscopic image of one frame. Accordingly, when the total frequencies belonging to the respective regions on the left and right sides of the dotted line L are compared, the total frequency belonging to the left side of the dotted line L, that is, the object region is larger than the total frequency belonging to the right side, that is, the direct line region. A histogram 29 is a histogram of an image having a low object region ratio in a fluoroscopic image of one frame. Accordingly, when the total frequencies belonging to the respective regions on the left and right sides of the dotted line L are compared, the total frequency belonging to the right side of the dotted line L, that is, the direct line region is larger than the total frequency belonging to the left side of the dotted line L, that is, the object region. A histogram is an intermediate image. Accordingly, the total frequencies belonging to the respective regions on the left and right sides of the dotted line L are almost equal.

Thus, since the magnitude of the ratio of the object region differs depending on an image, one value of $P_1$, $P_2$, and $P_3$ is applied according to the magnitude of the object ratio. The magnitude relationship of $P_1$, $P_2$, and $P_3$ is associated with the magnitude relationship of the object region ratio, and $P_1 > P_2 > P_3$ is satisfied. In this step, therefore, it is determined whether the object region ratio W (%) calculated in step S15 is equal to or higher than $X_1$ (corresponds to condition A), or equal to or higher than $X_2$ and less than $X_1$ (corresponds to condition B), or less than $X_2$ (corresponds to condition C). A $P_1$% threshold value is set if the object region ratio W (%) calculated in step S15 corresponds to the condition A, a $P_2$% threshold value is set if the object region ratio W (%) calculated in step S15 corresponds to the condition B, and a $P_3$% threshold value is set if the object region ratio W (%) calculated in step S15 corresponds to the condition C.

(Step S19)

The feedback brightness value calculation unit 6e calculates a reference brightness value $PV_{percent}$ by performing calculation processing based on the P tile method shown in the following Expression (4) using histogram data of the 16-bit fluoroscopic image data obtained in step S11 and one value of $P_1$, $P_2$, and $P_3$ set in steps S16 to S18. Then, the feedback brightness value calculation unit 6e calculates a feedback brightness value $PV_{ABS}$, which is used for the feedback, by applying the reference brightness value $PV_{percent}$ calculated in the following Expression (5) (S19).

First, the P tile method will be described. As shown in the following Expression (4), the P tile method is a method of binarization processing of image processing for calculating the reference brightness value $PV_{percent}$ when the ratio of the number of added pixels to the total number of pixels reaches P % by adding the number of pixels from the brightness value 0 in the histogram of one image.

$$P(\%) = (PC_{count} \div PC_{all}) \times 100 \quad (4)$$

P: set ratio (that is, one value of $P_1$, $P_2$, and $P_3$ set in steps S16 to S18)

$PC_{count}$: total number of pixels added from brightness value 0

$PC_{all}$: total number of pixels of one image

For example, in the case of an image having a high object region ratio, the left side of Expression (4) becomes the value of $P_1$. In addition, a brightness value when the ratio of the total number of pixels added from the brightness value 0 to the total number of pixels of one image becomes $P_1$ (%) is the reference brightness value $PV_{percent}$.

Then, the feedback brightness value calculation unit 6e calculates the feedback brightness value $PV_{ABS}$ by applying the calculated reference brightness value $PV_{percent}$ to the following Expression (5).

$$PV_{abs} = \frac{\sum_{k=0}^{k=PV_{percent}} (PC_k \times k)}{\sum_{k=0}^{k=PV_{percent}} PC_k} \quad (5)$$

$PV_{ABS}$: ABS feedback brightness value
K: arbitrary brightness value (0 to 16383)
$PC_k$: number of pixels at brightness value k
$PV_{percent}$: brightness value calculated by P tile method (Step S20)

The feedback brightness value calculation unit 6e transmits $PV_{ABS}$ calculated in step S19 to the X-ray control device 3 as an ABS feedback brightness value signal (hereinafter, referred to as a "feedback value signal"), and the feedback voltage calculation unit 3a in the X-ray control device 3 receives the ABS feedback brightness value signal. The feedback voltage calculation unit 3a converts the received ABS feedback brightness value $PV_{ABS}$ into a voltage fed back to the X-ray generator 2 (hereinafter, referred to as a "feedback voltage"). The X-ray condition determination unit 2a of the X-ray generator 2 compares the feedback voltage with a reference voltage set in advance. If the feedback voltage is lower than the reference voltage, the X-ray condition determination unit 2a adjusts the feedback voltage so as to match the reference voltage (for example, 5 V) by gradually increasing the current X-ray conditions (combination of the tube voltage and the tube current). On the contrary, if the feedback voltage is higher than the reference voltage, the X-ray condition determination unit 2a adjusts the feedback voltage so as to match the reference voltage (for example, 5 V) by gradually decreasing the current X-ray conditions (combination of the tube voltage and the tube current) (S20).

The conversion into the X-ray conditions from the feedback brightness value will be described with reference to FIG. 6. In FIG. 6, a reference voltage $Y_{ref}$ [V] is set, and it is determined that appropriate brightness adjustment is performed when the feedback voltage is equal to $Y_{ref}$ [V].

In FIG. 6, the feedback brightness value calculation unit 6e indicates $PV_{ABS}=X_1$ from the current fluoroscopic image (n-th frame), and the feedback voltage calculation unit 3a converts the feedback brightness value $X_1$ into a feedback voltage $Y_1$ [V] on the basis of $PV_{ABS}=X_1$. When $Y_1$ [V] is smaller than $Y_{ref}$ [V], the X-ray condition determination unit 2a compares the reference voltage $Y_{ref}$ [V] with the feedback voltage $Y_1$ [V] and increases the current X-ray condition ($mA_1$, $kV_2$) to ($mA_2$, $kV_2$) (where $mA_1 < mA_2$, $kV_1 < kV_2$). Then, an (n+1)-th fluoroscopic image is captured according to the new X-ray condition (mA, kV)=($mA_2$, $kV_2$). A feedback brightness value $PV_{ABS}=X_2$ calculated on the basis of the (n+1)-th frame is $Y_2$ [V] when converted into the feedback voltage. When $Y_2$ [V] and $Y_{ref}$ [V] are the same value ($Y_2$ [V]=$Y_{ref}$ [V]), the X-ray condition determination unit 2a determines that no X-ray condition change is required since the feedback voltage and the reference voltage are the same. Accordingly, an (n+2)-th frame is imaged under (mA, kV)= ($mA_2$, $kV_2$). As described above, the feedback brightness value $PV_{ABS}$ and the feedback voltage have a one-to-one correspondence, but the feedback brightness value $PV_{ABS}$ and the X-ray conditions (tube voltage, tube current) do not have a one-to-one correspondence.

The relationship between the feedback brightness value $PV_{ABS}$ and the X-ray conditions (tube voltage, tube current) will be described with reference to FIG. 7. When imaging objects having different thicknesses under the same X-ray conditions, the intensity of transmitted X-ray signals are different. Different feedback brightness values and different feedback voltages at different object thicknesses are shown. For example, in FIG. 7(a), when an object having an object thickness of 20 cm and an object having an object thickness of 10 cm are imaged under the same X-ray conditions (tube current, tube voltage)=($mA_{20}$, $kV_{20}$), a feedback brightness value $X_3$ and a feedback voltage $Y_3$ [V] are obtained for the former case, and a feedback brightness value $X_4$ and a feedback voltage $Y_4$ [V] are obtained for the latter case (where, $X_3 < X_4$, $Y_3$ [V] < $Y_4$ [V]).

Here, if the ABS (Automatic Brightness control System) functions such that fluoroscopic images obtained by imaging objects having different thicknesses indicate a fixed brightness value, the same feedback brightness value and the feedback voltage are shown at different object thicknesses, as shown in (b) of FIG. 7. That is, in order to make the transmitted X-ray intensity constant when the feedback brightness value $PV_{ABS}=X_3$ and the feedback voltage=$Y_3$ [V] are fixed, it is necessary to lower the X-ray intensity of the object having a relatively smaller object thickness. For this reason, it is necessary to lower the X-ray conditions for the object thickness of 10 cm rather than the X-ray conditions (tube current, tube voltage)=($mA_{20}$, $kV_{20}$) for the object thickness of 20 cm. Therefore, as the X-ray conditions, (tube current, tube voltage)=($mA_{10}$, $kV_{10}$) (where, $mA_{10} < mA_{20}$, $kV_{10} < kV_{20}$) is applied to the object having an object thickness of 10 cm.

Although the present embodiment has been described using a combination of tube current and tube voltage as the X-ray conditions, it is also possible to change the X-ray conditions by increasing or decreasing only the tube voltage or only the tube current.

(Step S21)

The X-ray generator 2 outputs the newly determined X-ray condition signal to the X-ray tube 1, and a fluoroscopic image of the (n+1)-th frame is captured according to the new X-ray conditions (S21).

For the effect of the ABS control according to the present embodiment, a case where the feedback brightness value $PV_{ABS}$ is lower than the target brightness value will be described as an example. In the present embodiment, when the feedback brightness value $PV_{ABS}$ is lower than the target brightness value, control is performed so as to increase the tube current and the tube voltage. The effect in this case will be described with reference to FIG. 8.

In a histogram 31 shown in (a) of FIG. 8, since the feedback brightness value $PV_{ABS}$ is lower than the target brightness value (in other words, since the feedback voltage is lower than the reference voltage), the width of the brightness of the pixel of the object region in the fluoroscopic image is narrow, and the brightness of the pixel of the direct line region is not relatively high either (less than 1000). The fluoroscopic image is captured by changing the X-ray conditions (for example, increasing the tube current and the tube voltage) so that the feedback brightness value $PV_{ABS}$ and the target brightness value of the histogram 31 match each other. In a histogram 32 (refer to FIG. 8 (b)) showing the distribution of brightness values of the fluoroscopic image, an overall shift to the high brightness side in the distribution of brightness values occurs and the distribution width of the brightness values shown in the histogram 32 spreads compared with the histogram 31.

In the conventional ABS, when changing a part for which fluoroscopic imaging needs to be performed, the shape, size, and the like of the ROI are changed for each part. However, according to the present embodiment, an object region on a histogram is detected for each fluoroscopic image without depending on the shape or size of the ROI, and a feedback brightness value to the ABS is calculated using the brightness value of the object region. Therefore, even when the object position is moved, it is possible to follow the X-ray conditions for the movement of the object position without requiring the work of the operator for resetting of the ROI. In addition, even when a region causing halation, such as a direct line region, is included in the fluoroscopic image, an object region can be imaged and displayed with the target brightness value without the influence of the direct line region. In addition, in the present embodiment, the feedback brightness value has been used as a brightness value representing the object region. However, it is also possible to set the average brightness value of the object region or the median value of the brightness value distribution of the object region as a representative value and determine the X-ray conditions so that the representative value matches the target brightness value.

Second Embodiment

In a second embodiment, as the values of $X_1$ and $X_2$ used in step S15 and the values of $P_1$, $P_2$, and $P_3$ set in steps S16 to S18 in the first embodiment, different values are given for each procedure and each part. This is because a target brightness value can be obtained by changing the X-ray conditions since the configuration of the histogram changes with a procedure or the brightness value is different if an object to be observed is different, such as a bone and an organ, even if the same procedure is used.

Third Embodiment

A third embodiment is an embodiment for reducing the influence of a metal when the metal is reflected in the object region. Specifically, Expression (4) used in the calculation of the P tile method performed in step S19 of the first embodiment is transformed into the following Expression (6).

$$P(\%) = \{PC_{count\ metal} \div (PC_{all} - PC_{under\ metal}) \times 100 \quad (6)$$

$PC_{count\ metal}$: total number of pixels added from brightness value $M_{threshold}$ $PC_{under\ metal}$: total number of pixels equal to or less than brightness value $M_{threshold}$ Here, $M_{threshold}$ is a metal threshold brightness value.

Figure 9:
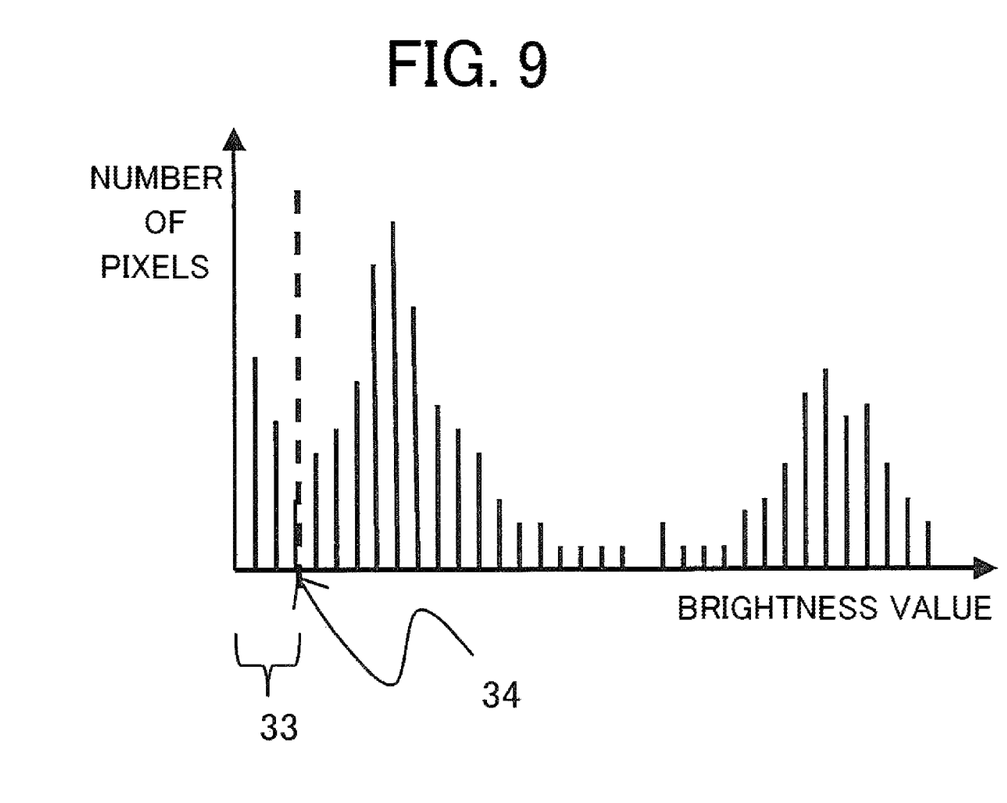
FIG. 9 is an explanatory diagram showing a histogram when the metal is mixed in the fluoroscopic image of one frame.

The third embodiment will be described with reference to FIG. 9. FIG. 9 is an explanatory diagram showing a histogram when metal is mixed in the fluoroscopic image of one frame. Since the metal is a material through which X-rays cannot be easily transmitted, a brightness value region 33 of the metal portion in the histogram has a low value. In such a case, when the P tile method is performed using Expression (4) described in the first embodiment, the brightness value of the pixel in which the metal is reflected is a calculation target in the feedback brightness value calculation. In this case, the feedback brightness value $PV_{ABS}$ is no longer appropriate value and the X-ray output is increased, resulting in an overexposed image. Therefore, by setting a metal threshold brightness value 34 (hereinafter, written as "$M_{threshold}$"), $PC_{count}$ is added from the brightness value $M_{threshold}$ in the calculation of the P tile method. As a result, since the metal included in the fluoroscopic image of one frame can be excluded from the feedback value calculation target, the feedback brightness value $PV_{ABS}$ is calculated as an appropriate value that is not influenced by the metal.

Fourth Embodiment

A fourth embodiment is an embodiment for excluding the brightness value of the pixel, in which an X-ray aperture is reflected, of the fluoroscopic image from pixels, for which the feedback brightness value $PV_{ABS}$ is to be calculated, using position information of the X-ray aperture for limiting an X-ray irradiation field region in addition to the first embodiment. When the X-ray aperture is placed in the X-ray tube 1, an effective image portion in the fluoroscopic image of one frame is the inner side of a region where the X-ray aperture is imaged in the fluoroscopic image. In the first embodiment, however, since all pixels in the fluoroscopic image of one frame are feedback targets of the ABS, a portion of the aperture inserted into the X-ray irradiation field is erroneously recognized as an object region. Due to the effect, the feedback brightness value $PV_{ABS}$ fed back to the ABS is no longer appropriate value (value is low). As a result, it is not possible to perform appropriate ABS control.

Therefore, an aperture position detection device 8a that detects the actual position information of the X-ray aperture attached to the X-ray tube 1 is provided in the system control device 8 in advance. The histogram generation unit 6b calculates the position of a region where the X-ray aperture is imaged in the fluoroscopic image of one frame, which has been generated by the image generation unit 6a, using the actual position information. Then, the histogram generation unit 6b generates a histogram using an image on the inner side than the region where the X-ray aperture is imaged in the fluoroscopic image, and performs processing from step S12.

According to the present embodiment, since the feedback brightness value $PV_{ABS}$ can be calculated in a state where pixels of the region where the X-ray aperture is imaged are excluded, it is also possible to perform appropriate ABS control for the fluoroscopic image in which the aperture is placed.

REFERENCE SIGNS LIST

1: X-ray tube
2: X-ray generator
3: X-ray control device
4: X-ray plane detector
5: X-ray plane detector control device
6: image processing device
7: image display device
8: system control device
9: table
10: X-ray-fluoroscopic apparatus

The invention claimed is:

1. An X-ray image diagnostic apparatus, comprising:
an X-ray generator that generates X-rays according to X-ray conditions defining an output of X-rays;
an X-ray detector that detects X-rays transmitted through an object and outputs a transmitted X-ray signal;
an image generation calculator that generates an X-ray image of the object on the basis of the transmitted X-ray signal;
a histogram generation calculator that generates a histogram showing a distribution of brightness values of the X-ray image;
an object region detection calculator that detects an object region, which is a region where the object is imaged, in the X-ray image on the basis of the histogram; and
an X-ray condition determination calculator that determines the X-ray conditions so that a brightness value representing the object region approaches a target brightness value of the object region set in advance;
a feedback brightness value calculator that sets, as a reference brightness value, a brightness value when a ratio of the total number of pixels summed up from a minimum brightness value in the histogram to the total number of pixels of the histogram reaches a second threshold value set in advance and calculates, as a feedback brightness value, a value obtained by dividing a sum of values, which are obtained by multiplying respective brightness values from the minimum brightness value to the reference brightness value by the number of pixels of the corresponding brightness value, by a sum of the number of pixels from the minimum brightness value to the reference brightness value;
wherein the X-ray generator generates the X-rays according to the determined X-ray conditions; and
wherein the X-ray condition determination calculator determines the X-ray conditions so that the feedback brightness value matches the target brightness value.

2. The X-ray image diagnostic apparatus according to claim 1, further comprising:
an object region ratio calculator that calculates a ratio of the number of pixels of the object region to the total number of pixels of the histogram,
wherein the feedback brightness value calculator determines which of at least two or more image types having different object region ratios the X-ray image corresponds to according to the calculated object region ratio, and determines the second threshold value according to each image type.

3. The X-ray image diagnostic apparatus according to claim 2, wherein the second threshold value according to each image type is determined according to at least one of a procedure of capturing the X-ray image or a part for which the X-ray image is to be captured.

4. The X-ray image diagnostic apparatus according to claim 1,
wherein the feedback brightness value calculator calculates the feedback brightness value with a brightness value of a region where a metal is imaged in the histogram as the minimum brightness value.

5. The X-ray image diagnostic apparatus according to claim 1, further comprising:
a feedback voltage calculator that calculates a feedback voltage by converting the feedback brightness value into a voltage,
wherein the X-ray condition determination calculator compares a reference voltage, which is obtained by converting the target brightness value into a voltage, with the feedback voltage, and changes the X-ray conditions so that the output of the X-rays is increased when the feedback voltage is lower than the reference voltage and changes the X-ray conditions so that the output of the X-rays is reduced when the feedback voltage is higher than the reference voltage.

6. The X-ray image diagnostic apparatus according to claim 1, wherein the object region detection calculator divides the histogram into two data groups with an arbitrary brightness value as a boundary, sets, as a first threshold value, a brightness value when an inter-class variance of two classes of the respective data groups or an index value increasing or decreasing in association with the inter-class variance is maximized, and detects a data group less than the first threshold value as the object region.

7. The X-ray image diagnostic apparatus according to claim 6,
wherein the histogram generation calculator generates a processed histogram by performing at least one of processing of reducing a gradation to the arbitrary number of bits, which is less than the number of bits of the X-ray image, and processing of thinning out a histogram generated from the X-ray image by a predetermined brightness value; and
wherein the object region detection calculator detects the object region using the processed histogram.

8. A method for controlling an X-ray generation device, comprising:
a step of generating a histogram showing a distribution of brightness values of an X-ray image of an object;
a step of detecting an object region, which is a region where the object is imaged, in the X-ray image on the basis of the histogram; and
a step of determining X-ray conditions defining an output of X-rays so that a brightness value representing the object region approaches a target brightness value of the object region set in advance;
a step of setting, as a reference brightness value, a brightness value when a ratio of the total number of pixels summed up from a minimum brightness value in the histogram to the total number of pixels of the histogram reaches a second threshold value set in advance and calculates, as a feedback brightness value, a value obtained by dividing a sum of values, which are obtained by multiplying respective brightness values from the minimum brightness value to the reference brightness value by the number of pixels of the corresponding brightness value, by a sum of the number of pixels from the minimum brightness value to the reference brightness value; and wherein the step of determining X-ray condition, includes a step of determining the X-ray conditions so that the feedback brightness value matches the target brightness value.

* * * * *